(12) United States Patent
Xu et al.

(10) Patent No.: US 8,349,258 B2
(45) Date of Patent: Jan. 8, 2013

(54) SENSOR AND METHOD FOR MEASURING AMOUNT OF ANALYTE IN HUMAN INTERSTITIAL FLUID, FLUID CHANNEL UNIT

(75) Inventors: Kexin Xu, Tianjin (CN); Dachao Li, Tianjin (CN)

(73) Assignee: Tianjin Sunshine Optics Technologies Co., Ltd., Tianjin (CN)

( * ) Notice: Subject to any disclaimer, the term of this patent is extended or adjusted under 35 U.S.C. 154(b) by 385 days.

(21) Appl. No.: 12/867,964

(22) PCT Filed: Nov. 26, 2008

(86) PCT No.: PCT/CN2008/001933
§ 371 (c)(1), (2), (4) Date: Aug. 17, 2010

(87) PCT Pub. No.: WO2009/103197
PCT Pub. Date: Aug. 27, 2009

(65) Prior Publication Data
US 2010/0307929 A1    Dec. 9, 2010

(30) Foreign Application Priority Data
Feb. 21, 2008 (CN) .......................... 2008 1 0057935

(51) Int. Cl.
*G01N 33/00* (2006.01)
(52) U.S. Cl. ................. 422/68.1; 422/82.05; 422/82.02; 436/149
(58) Field of Classification Search ............. 422/68.1, 422/82.05, 82.02
See application file for complete search history.

(56) References Cited

U.S. PATENT DOCUMENTS
5,578,976 A * 11/1996 Yao .............................. 333/262
(Continued)

FOREIGN PATENT DOCUMENTS
CN     1372135 A    10/2002
(Continued)

OTHER PUBLICATIONS
"Bioassay of Glutathione S-transferase (GST) Antibody-antigen Interactions Using Microcantilever Sensor"; Xue et al.' Journal of Experimental Mechanics, vol. 22, No. 3-4, Aug. 2007; 6 pages.
(Continued)

*Primary Examiner* — Sam P Siefke
(74) *Attorney, Agent, or Firm* — Westman, Champlin & Kelly, P.A.

(57) ABSTRACT

Disclosed is a sensor for measuring the amount of an analyte to be detected in human interstitial fluid, comprising a micro-cantilever sensing unit which includes: a first substrate; a micro-cantilever which is substantially in parallel with the first substrate and one end of which is supported onto the first substrate; a gold film formed onto at least one side of the micro-cantilever; a protein layer formed on the gold film, the protein layer being used to adsorb, at a surface thereof, the analyte to be detected in human interstitial fluid; a driving electrode provided on the first substrate; a micro-cantilever electrode which is provided on the first substrate at a position where the micro-cantilever is supported, and which is cooperated with the driving electrode so as to drive the micro-cantilever to produce resonance in a direction perpendicular to the first substrate; and a detecting electrode which is provided on the first substrate and which is cooperated with the micro-cantilever electrode so as to detect resonance frequency of the micro-cantilever. The present invention also relates to a fluid channel unit, a sensor system, and a method for measuring the amount of an analyte to be detected in human interstitial fluid.

15 Claims, 2 Drawing Sheets

U.S. PATENT DOCUMENTS

| | | | |
|---|---|---|---|
| 6,016,686 A * | 1/2000 | Thundat | 73/23.2 |
| 6,523,392 B2 | 2/2003 | Porter et al. | 73/24.01 |
| 8,115,693 B2 * | 2/2012 | Salsman et al. | 343/703 |
| 8,258,899 B2 * | 9/2012 | Feng et al. | 335/78 |
| 2002/0018334 A1 | 2/2002 | Hill et al. | |
| 2003/0032293 A1 | 2/2003 | Kim et al. | |
| 2007/0095129 A1 | 5/2007 | Donaldson et al. | 73/53.01 |
| 2007/0182419 A1* | 8/2007 | Ushijima et al. | 324/457 |
| 2010/0206073 A1* | 8/2010 | Kaminishi et al. | 73/504.12 |

FOREIGN PATENT DOCUMENTS

| | | |
|---|---|---|
| CN | 1844897 | 5/2006 |
| CN | 1866007 A | 11/2006 |
| EP | 1 536 227 A2 | 6/2005 |

OTHER PUBLICATIONS

International Search Report and Written Opinion in corresponding application PCT/CN2008/001933, dated Mar. 5, 2009.

* cited by examiner

SENSOR AND METHOD FOR MEASURING AMOUNT OF ANALYTE IN HUMAN INTERSTITIAL FLUID, FLUID CHANNEL UNIT

CROSS-REFERENCE OF RELATED APPLICATION

This application is a Section 371 National Stage Application of International Application No. PCT/PCT/CN2008/001933, filed Nov. 26, 2008 and published as WO2009/103197 on Aug. 27, 2009, in English, which claims the benefit of Chinese Patent Application No. 200810057935.8 filed before the State Intellectual Property Office of China on Feb. 21, 2008, the contents of which are hereby incorporated by reference in their entirety.

BACKGROUND OF THE INVENTION

1. Field of Invention

The present invention relates to a sensing system for measuring the amount of an analyte to be detected in human interstitial fluid, more particularly, to a resonance-type micro-cantilever sensor for measuring the concentration (or the amount) of an analyte to be detected, such as glucose, in the human interstitial fluid, a fluid channel unit used together with the resonance-type micro-cantilever sensor, a method for measuring the concentration (or the amount) of an analyte to be detected, such as glucose, in the human interstitial fluid by using the fluid channel unit and the resonance-type micro-cantilever sensor, and a sensor system for sensing the amount of an analyte to be detected, such as glucose, in the human interstitial fluid.

2. Description of the Related Art

Diabetes is a common and frequently-occurring disease for the middle-aged and elderly people, and the incidence thereof is increasing with improved living standards. In addition, diabetes, cancer, and cardio-cerebrovascular disease are considered by WHO as the three difficult diseases in the world.

According to the estimation by WHO, the total number of the diabetics in the world is about 170 millions (including 30 millions in China) now, and will increase to 300 millions by 2025. Diabetes has already become one of the ten main causes of death in Asia, and more lives are threatened by it than by infectious diseases. Therefore, it is extremely necessary to take measures to prevent and treat diabetes, and accurate measurement of the glucose concentration in the blood is one of the keys thereto.

The measurement of the glucose concentration in the blood is performed mainly by using the following three methods: an invasive detecting method, a minimally invasive detecting method, and a non-invasive detecting method. At present, the measurement is carried out mostly by using the invasive detecting method in which first, blood is sampled from a finger of a patient, then, the glucose concentration in the blood is detected with chemical methods, for instance, by using enzyme electrodes. In the invasive detecting method, however, expendable material is used, and also the patient has to suffer a certain injury which may bring the patient pain and a risk of being infected. Moreover, the most serious disadvantage of the invasive detecting method lies in that the glucose concentration in the blood can not be measured dynamically and thus the change of the glucose concentration can not be reflected in real time, therefore, the glucose concentration obtained by the invasive detecting method is not proper to be used as excellent reference information. Specifically, the measurement obtained by periodically sampling blood from a finger usually can not reveal all hypoglycemia and hyperglycemia, especially nightly hypoglycemia.

Accordingly, a dynamic, continuous and real-time measurement of the glucose concentration in the blood will greatly promote clinical prevention and treatment of diabetes.

Non-invasive detecting techniques under developed for measuring the glucose concentration in the blood mainly comprise a series of optical methods including near infrared spectroscopy, middle infrared spectroscopy, Raman spectroscopy, polarimetry and the like. When the glucose concentration in the blood is measured by using these methods no injury is produced, which represents a development direction. However, the non-invasive detecting techniques are still under preclinical study phase because of the disadvantages thereof such as low measuring accuracy and low reliability.

In view of the above defects and disadvantages of the invasive and non-invasive detecting techniques, much attention has been paid recently to the minimally invasive detecting method in which the glucose concentration in the blood is detected by extracting the human interstitial fluid and then measuring accurately the glucose concentration in the human interstitial fluid. The minimally invasive detecting method is based on an elementary principle that there is high correlation between the glucose concentration in the blood and that in the human interstitial fluid. In the so-called minimally invasive detecting method, first, the tissue fluid is extracted, with a painless and minimal incision, from the skin surface of a patient, then the glucose concentration in the human interstitial fluid is detected with accuracy, finally, the glucose concentration in the blood is predicted precisely according to the correlation between the glucose concentration in the blood and that in the human interstitial fluid. In addition, because methods, such as low-frequency ultrasonic transdermal treatment and reverse ion electro-osmosis, are used, continuously extracting the human interstitial fluid in the skin is obtained. The minimally invasive detecting method is of great practical significance to achieve dynamical and continuous measurement of the glucose concentration in the blood.

However, since there are various chemicals and trace elements in the human interstitial fluid, how to detect the trace glucose in the human interstitial fluid with selectivity and accuracy is the key to the minimally invasive detecting method. Further, because the patient has to carry with a minimally invasive detecting device all the time in order to perform dynamic and real-time measurement on the glucose concentration in the blood, miniaturization of the minimally invasive detecting device is necessary. Concerning the above, a miniaturized sensor for measuring accurately the amount of the trace glucose in the tissue fluid is the core of the minimally invasive detecting method.

SUMMARY OF INVENTION

Considering the above defects in the prior art, the present invention is directed to a sensor for measuring the amount of an analyte to be detected in human interstitial fluid, and the sensor can detect selectively and accurately the concentration of the analyte to be detected in the human interstitial fluid while meeting the requirements of clinically and minimally invasive detecting the glucose in the blood.

The present invention provides a sensor for measuring the amount of an analyte to be detected in human interstitial fluid, the sensor comprising a resonance-type micro-cantilever on which D-Galactose/D-Glucose Binding Protein (GGBP) is bound, and being capable of detecting the trace glucose in the human interstitial fluid with selectivity and accuracy.

According to one aspect of the present invention, a sensor for measuring the amount of an analyte to be detected in human interstitial fluid is provided, the sensor comprises a micro-cantilever sensing unit which includes: a first substrate; a micro-cantilever which is substantially in parallel with the first substrate and one end of which is supported onto the first substrate; a gold film formed onto at least one side of the micro-cantilever; a protein layer formed on the gold film and used to adsorb, at a surface thereof, the analyte to be detected in human interstitial fluid; a driving electrode provided on the first substrate; a micro-cantilever electrode which is provided on the first substrate at a position where the micro-cantilever is supported, and which is cooperated with the driving electrode so as to drive the micro-cantilever to produce resonance in a direction perpendicular to the first substrate; and a detecting electrode provided on the first substrate and cooperated with the micro-cantilever electrode to detect resonance frequency of the micro-cantilever.

In the above sensor, the gold film may be formed on a surface of one side of the micro-cantilever opposite to the other side thereof facing the first substrate.

In the above sensor, alternatively, the gold film is deposited, by means of a sputtering process or an evaporation process, on the surface of the micro-cantilever made of silicon.

In the above sensor, alternatively, the protein layer comprises D-Galactose/D-Glucose Binding Protein for selectively adsorbing glucose molecules in the human interstitial fluid.

In the above sensor, alternatively, the protein layer is adhered to a surface of the gold film by amine coupling or mercaptan coupling.

In the above sensor, alternatively, between the other side of the micro-cantilever facing the first substrate and the detecting electrode is formed a parallel plate capacitor.

According to another aspect of the present invention, a fluid channel unit is also provided, wherein the fluid channel unit is used together with the sensor so that the human interstitial fluid is adsorbed evenly to the surface of the gold film.

Specifically, the fluid channel unit according to the present invention comprises a second substrate; and a fluid channel formed on the second substrate, wherein human interstitial fluid to be detected flows through the fluid channel in a way that the protein layer of the sensor for measuring the amount of an analyte to be detected in the human interstitial fluid is brought in at least partial contact with a surface of the human interstitial fluid so that human interstitial fluid molecules of the human interstitial fluid are adsorbed onto the surface of the protein layer.

In the above fluid channel unit, alternatively, the surface of the gold film may be brought in at least partial contact with protein solution flowing in the fluid channel so as to form the protein layer on the gold film.

According to a further aspect of the present invention, a method for measuring the amount of an analyte to be detected in human interstitial fluid is provided, and the method comprises steps of:

measuring a natural resonant frequency of the micro-cantilever of the sensor for measuring the amount of an analyte to be detected in human interstitial fluid, comprising steps of:

applying a voltage application step in which an AC driving voltage between the driving electrode and the micro-cantilever electrode to drive the micro-cantilever to vibrate in the direction perpendicular to the first substrate;

measuring a change of capacitance between the detecting electrode on the first substrate and the micro-cantilever electrode in real time during the micro-cantilever vibrates; and determining the driving frequency of the AC driving voltage at which the change of the capacitance is maximal as a first resonance frequency $f_0$ of the micro-cantilever by adjusting a driving frequency of the AC driving voltage and repeating the capacitance measurement step, and;

adsorbing human interstitial fluid molecules of the human interstitial fluid onto the surface of the protein layer by bring fluid containing the human interstitial fluid in contact with the surface of the protein layer;

measuring a second resonance frequency $f_1$ of the micro-cantilever on which the human interstitial fluid molecules have been adsorbed by repeating the applying voltage step, the measuring capacitance step and the determining resonance frequency step; and calculating the amount of the analyte to be detected in the human interstitial fluid based on the first resonance frequency $f_0$ and the second resonance frequency $f_1$.

In the above method, alternatively, in the adsorbing step, the human interstitial fluid passes the protein layer in the flow channel of the fluid channel unit.

The above method may further comprise a protein layer forming step which includes steps of: guiding a first chemical solution for activating a surface of the gold film into the fluid channel; flowing the first chemical solution through the surface of the gold film so as to activate the surface of the gold film and form a self-assembling molecule layer via Au—S bonds; guiding a second chemical solution for surface coupling and D-Galactose/D-Glucose Binding Protein into the fluid channel respectively; at the self-assembling molecule layer, securing the D-Galactose/D-Glucose Binding Protein to the activated surface of the gold film by using amine coupling or mercaptan coupling.

In the above method, alternatively, the D-Galactose/D-Glucose Binding Protein is a protein that adsorbs glucose molecules with selectivity.

Alternatively, the method further comprises a protein synthesis step of forming the D-Galactose/D-Glucose Binding Protein, including:

performing site-directed mutation on encoding gene mg1B of the D-Galactose/D-Glucose Binding Protein of *escherichia coli*, wherein the mutation is actualized at E149 mutation site only, or both at E149C mutation site and at A213S mutation site, or simultaneously at E149, A213 and L238 mutation sites;

constructing a gene engineering strain which over-expresses wild type D-Galactose/D-Glucose Binding Protein of the *escherichia coli* and mutation type D-Galactose/D-Glucose Binding Protein of the *escherichia coli;* fermenting the constructed gene engineering strain by using a shake flask so that the D-Galactose/D-Glucose Binding Protein is expressed stably; and separating and purifying the D-Galactose/D-Glucose Binding Protein from fermenting products.

According to still another aspect of the present invention, a sensor system for sensing the amount of an analyte to be detected in human interstitial fluid is provided, and the sensor system comprises the sensor for measuring the amount of the analyte to be detected in the human interstitial fluid; and the fluid channel unit.

Alternatively, the sensor system further comprises: at least two first self-alignment holes formed at two opposite ends of the first substrate; at least two second self-alignment holes formed at two opposite ends of the second substrate and corresponding to the first self-alignment holes respectively; and a plurality of support posts which are provided respectively within the self-alignment holes so that the sensor having the micro-cantilever is supported on the fluid channel unit and that protein solution flowing in the fluid channel is maintained to be in at least partial contact with a surface of the gold film.

The present invention relates to a glucose sensor system having a resonance-type micro-cantilever on which the D-Galactose/D-Glucose Binding Protein is bound. This sensor system comprises a resonance-type micro-cantilever sensing unit and a micro fluid channel unit. In measurement, with the micro fluid channel unit, the human interstitial fluid to be detected passes a surface of the resonance-type micro-cantilever sensing unit, and the sensing unit detects the amount of an analyte to be detected, such as glucose, in the human interstitial fluid. The resonance-type micro-cantilever sensing unit and the micro fluid channel unit can be integrated together by micromachining, for instance, by bonding, so that a sensor structure having two layers is formed. The resonance-type micro-cantilever sensing unit comprises a micro-cantilever and a substrate on which the micro-cantilever is provided, wherein the micro-cantilever is of a sandwich structure comprising three layers of a silicon micro-cantilever, a gold film and D-Galactose/D-Glucose Binding Protein, and wherein a driving electrode and a detecting electrode for the micro-cantilever are integrated on the substrate. The micro fluid channel unit comprises a sample inlet, a micro fluid channel, and a sample outlet, wherein the sample inlet and the sample outlet provide joints for guiding the fluid to be detected into and out of the micro fluid channel.

The operation principle of the glucose sensor having a resonance-type micro-cantilever on which the D-Galactose/D-Glucose Binding Protein is bound is as follows:

by using the D-Galactose/D-Glucose Binding Protein bound on the micro-cantilever, trace glucose in the human interstitial fluid can be adsorbed selectively;

by combining electrostatic actuation with capacitance measurement, a resonance is induced in the micro-cantilever in a perpendicular direction;

by calculating the difference between the resonance frequencies of the micro-cantilever before and after glucose molecules are adsorbed to a surface of the micro-cantilever, the mass of the glucose molecules adsorbed to the surface of the micro-cantilever is detected.

In addition, the solutions of the present invention can produce at least one of the following technical effects:

the glucose molecules in the human interstitial fluid are adsorbed selectively by the D-Galactose/D-Glucose Binding Protein which shows good specificity, thus, adverse affection or interference on the glucose measurement due to other chemical constituents and trace elements in the human interstitial fluid can be suppressed greatly or even be removed; and thus, the using of the bound D-Galactose/D-Glucose Binding Protein has advantages in lifetime over the using of conventional enzyme electrodes and the like;

by using resonance, the mass of the glucose molecules adsorbed on the surface of the micro-cantilever sensor is measured with high precision; and it is proved by theoretical analysis and calculation that the mass resolution of the sensor of the present invention can be improved, by using a proper structure of the sensor and proper driving electronic circuits, to be an order of fg ( ) so as to meet the requirements of the minimally invasive detecting method;

a micro-cantilever structure is used in the present invention, thus, the sensor according to the present invention has a simple structure, a small volume, a light weight, and can be integrated easily with the micro fluid channel; in addition, fewer peripheral components for the sensor are used, driving and detecting circuits for the sensor are simple, and the amount of the human interstitial fluid to be detected is small; both the micro-cantilever sensor unit and the fluid channel unit can be manufactured in a mass production and simple manner by micromachining, which results in a low production cost.

BRIEF DESCRIPTION OF THE DRAWING

These and/or other aspects and advantages of the invention will become apparent and more readily appreciated from the following description of the embodiments, taken in conjunction with the accompanying drawings of which.

DETAILED DESCRIPTION OF PREFERRED EMBODIMENTS

Figure 1:
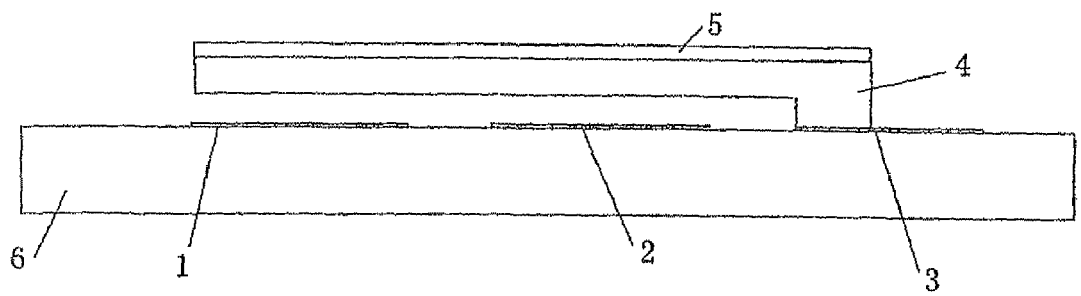
FIG. 1 is a section view schematically showing the structure of a micro-cantilever sensor according to one embodiment of the present invention, wherein D-Galactose/D-Glucose Binding Protein is not bound to the micro-cantilever sensor.

Preferred embodiments of the present invention will be described hereinafter in detail with reference to the attached drawings, wherein the like reference numerals refer to the like elements throughout the specification. These embodiments should not be construed as being limited to the embodiment set forth herein, rather for illustrative purpose.

The structure of a micro-cantilever sensor for measuring the amount of an analyte to be detected in human interstitial fluid according to one exemplary embodiment of the present invention will be illustrated below in connection with FIG. 1, wherein D-Galactose/D-Glucose Binding Protein is not bound to the micro-cantilever sensor.

Referring to FIG. 1, the sensor comprises a micro-cantilever sensing unit which includes: a first substrate 6 used as a base; a micro-cantilever 4 which is substantially in parallel with the first substrate 6 and one end of which is supported onto the first substrate 6; a gold film 5 formed onto at least one side of the micro-cantilever 4, and in one exemplary embodiment, the gold film 5 is formed on a surface of one side of the micro-cantilever 4 opposite to the other side thereof facing the first substrate 6, that is, the side on which the gold film 5 is formed is opposite to the first substrate 6; a driving electrode 1 provided on the first substrate 6; a micro-cantilever electrode 3 which is provided on the first substrate 6 at a position where the micro-cantilever 4 is supported, that is, at a position where the micro-cantilever 4 contacts with the first substrate 6, and which is cooperated with the driving electrode 1 so as to drive the micro-cantilever 4 to produce resonance in a direction perpendicular to the first substrate 6; and a detecting electrode 2 which is provided on the first substrate 6 and which is cooperated with the micro-cantilever electrode 3 so as to detect resonance frequency of the micro-cantilever 4. In one exemplary embodiment of the present invention, the whole micro-cantilever 4 may be in a L-shape, thus, the micro-cantilever 4 is suspended on the first substrate 6 by the one end thereof, thus, a parallel plate capacitor is formed between the other side of the micro-cantilever 4 facing the first substrate 6 and the detecting electrode 2. In one exemplary embodiment of the present invention, an integrated micro sensor, comprising the first substrate 6, the driving electrode 1, the detecting electrode 2, the micro-cantilever 4 made of for example silicon material, and the gold film 5 for binding D-Galactose/D-Glucose Binding Protein, can be manufactured by micromachining.

Figure 2:
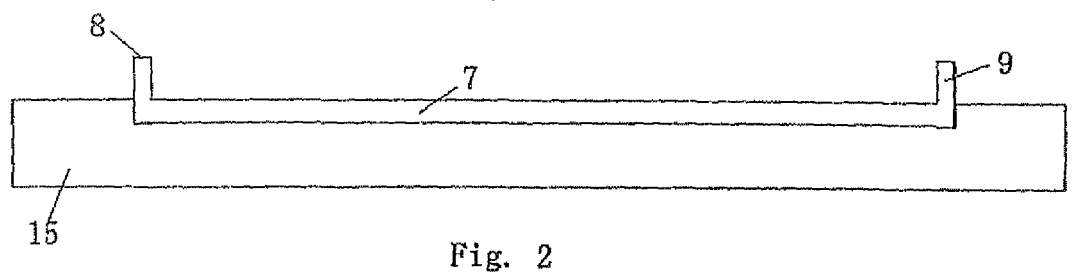
FIG. 2 is a section view schematically showing the structure of a micro fluid channel unit according to one embodiment of the present invention.

FIG. 2 is a section view schematically showing the structure of a micro fluid channel unit according to one exemplary embodiment of the present invention. The fluid channel unit comprises: a second substrate 15; and a micro fluid channel 7 formed on the second substrate 15. The micro fluid channel unit 7 comprises a sample inlet 8, and a sample outlet 9, which provide ports for guiding the fluid to be detected into and out of the micro fluid channel 7, respectively. In an exemplary embodiment of the present invention, the micro fluid channel unit cooperating with the sensor can be produced directly by micromachining. In the present invention, the micro fluid channel unit functions both to bind a D-Galactose/D-Glucose Binding Protein layer 11 to a surface of the gold film 5 of the sensor unit and to adsorb molecules to be detected in the human interstitial fluid, such as glucose molecules to the D-Galactose/D-Glucose Binding Protein layer 11 so that a glucose molecule layer 13 is formed on the D-Galactose/D-Glucose Binding Protein layer 11 (referring to FIGS. 4 and 6).

Figure 3:
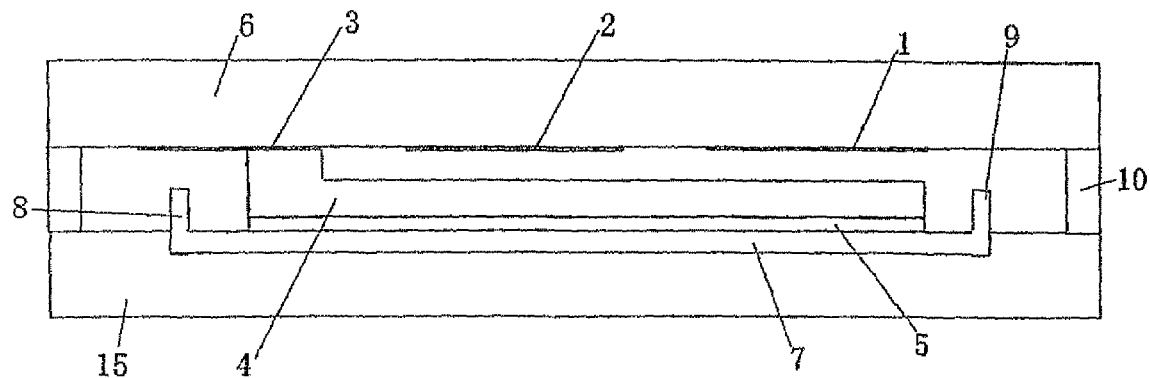
FIG. 3 is a section view schematically showing that the micro-cantilever sensor in FIG. 1 and the micro fluid channel unit in FIG. 2 are integrated to bind the D-Galactose/D-Glucose Binding Protein onto a surface of a gold film of the sensor.

The process of binding the D-Galactose/D-Glucose Binding Protein to the surface of the gold film 5 will be described with reference to FIG. 3. It should be noted that FIG. 3 is a schematic section view showing that the micro-cantilever sensor in FIG. 1 and the micro fluid channel unit in FIG. 2 are integrated. Specifically, in FIG. 3, the micro-cantilever sensor in FIG. 1 is overturned and thus the micro-cantilever 4 is positioned underneath the first substrate 6, and this overturned micro-cantilever sensor at an upper position is placed on the fluid channel unit in FIG. 2 at a lower position.

Figure 7:
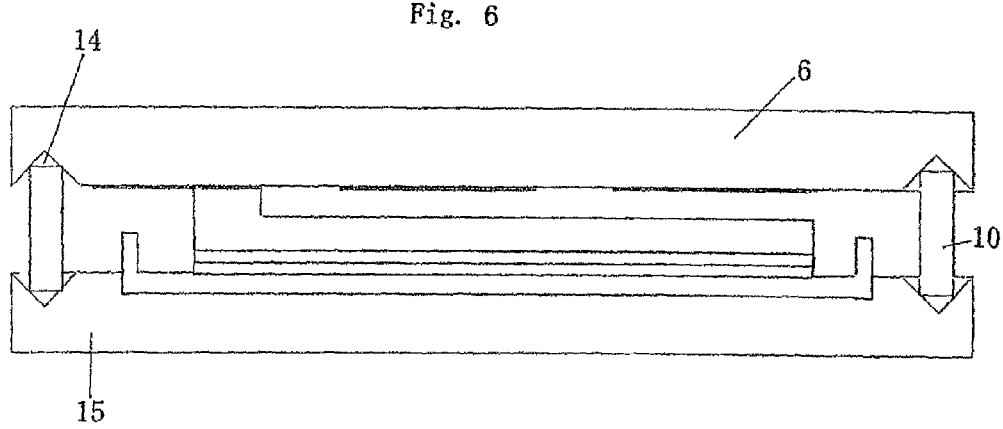
FIG. 7 is a view schematically showing the structure of a self-location assembling structure used to integrate the micro-cantilever sensor and the micro fluid channel unit.

In one exemplary embodiment of the present invention, referring to FIG. 7, through V-shape self-alignment holes 14 formed on the first substrate 6 of the micro-cantilever sensor and the second substrate 15 of the fluid channel unit, the micro-cantilever sensor and the fluid channel unit are assembled together. These V-shape self-alignment holes 14 may be formed by micromachining through an anisotropic vetch-stop technique. In addition, by providing support posts 10 having a predetermined length between the first substrate 6 and the second substrate 15, the surface of the gold film 5 is in close contact with a surface of the micro fluid channel 7.

Figure 6:
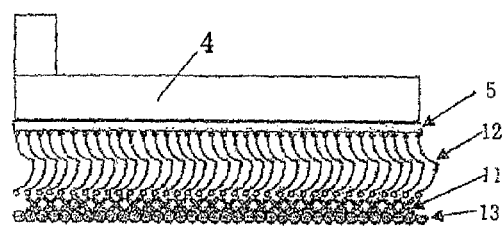
FIG. 6 is an enlarged view schematically showing substance distribution on an upper surface of the micro-cantilever sensor after the glucose molecules are adsorbed.

Further referring to FIG. 3, a chemical solution for activating the surface of the gold film 5 is guided into the micro fluid channel 7 by a micro-pump in a way that the chemical solution passes the surface of the gold film 5 at a stable or constant speed so as to activate the surface of the gold film 5 of the micro-cantilever sensor and form a self-assembling molecule layer via Au—S bonds 12 (referring to FIG. 6). The micropump may be used to guide the chemical solution for surface coupling and the D-Galactose/D-Glucose Binding Protein into the micro fluid channel 7, respectively. At a surface of the self-assembling molecule layer, the D-Galactose/D-Glucose Binding Protein is secured to the activated surface of the gold film 5 of the micro-cantilever sensor by using a coupling method such as an amine coupling method or a mercaptan coupling, and thus, the sensor structure shown in FIG. 4, in which the D-Galactose/D-Glucose Binding Protein has been bound to the micro-cantilever sensor, is formed.

It is noted that the D-Galactose/D-Glucose Binding Protein showing good specificity and used for adsorbing selectively the glucose molecules is synthesized by using biotechnology, and the synthesizing method comprises the following steps:

(1) performing site-directed mutation on encoding gene mg1B of the D-Galactose/D-Glucose Binding Protein of *escherichia coli*, wherein the mutation is actualized at E149 mutation site only, or both at E149C mutation site and at A213S mutation site, or simultaneously at E149, A213 and L238 mutation sites;

(2) constructing a gene engineering strain which overexpresses wild type D-Galactose/D-Glucose Binding Protein of the *escherichia coli* and mutation type D-Galactose/D-Glucose Binding Protein of the *escherichia coil*;

(3) fermenting the constructed gene engineering strain by using a shake flask so that the D-Galactose/D-Glucose Binding Protein is expressed stably and with high quality; and (4) separating and purifying the D-Galactose/D-Glucose Binding Protein from fermenting products so that the purity of the obtained D-Galactose/D-Glucose Binding Protein is more than 95%.

According to another aspect of the present invention, a method for measuring the amount of an analyte to be detected in the human interstitial fluid is disclosed, and the method comprises steps of:

measuring a natural resonant frequency of the micro-cantilever of the sensor for sensing the amount of an analyte to be detected in the human interstitial fluid, comprising steps of:

applying an AC driving voltage between the driving electrode 1 and the micro-cantilever electrode 3 so that the micro-cantilever 4 vibrates in the direction perpendicular to the first substrate 6;

measuring a change of capacitance between the detecting electrode 2 on the first substrate 6 and the micro-cantilever electrode 3 in real time during the micro-cantilever 4 vibrates; and determining the driving frequency of the AC driving voltage at which the change of the capacitance is maximal as a first resonance frequency $f_0$ of the micro-cantilever 4 through adjusting a driving frequency of the AC driving voltage and repeating the capacitance measurement step;

bringing fluid containing the human interstitial fluid in contact with the surface of the protein layer 11 so that human interstitial fluid molecules of the human interstitial fluid are adsorbed onto the surface of the protein layer 11;

measuring a second resonance frequency $f_1$ of the micro-cantilever 4 on which the human interstitial fluid molecules have been adsorbed through repeating the applying voltage step, the measuring capacitance step and the determining first resonance frequency step; and calculating the amount of the analyte to be detected in the human interstitial fluid based on the first resonance frequency $f_0$ and the second resonance frequency $f_1$.

The operation principle of the glucose sensor having a resonance-type micro-cantilever on which D-Galactose/D-Glucose Binding Protein is bound is that: after the surface of the micro-cantilever 4 adsorbs selectively the glucose molecules by using the D-Galactose/D-Glucose Binding Protein, the resonance frequency of the micro-cantilever will alter.

The resonance frequency of the micro-cantilever 4 may be expressed by $$f = \frac{1}{2\pi}\sqrt{\frac{k}{m_{eff}}} \quad (1)$$

wherein $m_{eff}$ is the effective mass of the micro-cantilever, k is the elastic constant of the micro-cantilever which may be expressed by $$k = \frac{E}{4}\frac{w^3}{l^3}t \quad (N/m) \quad (2)$$

wherein E is Young Modulus of the micro-cantilever 4, and w, l and t are width, length and thickness of the micro-cantilever 4 respectively.

After the surface of the micro-cantilever 4 adsorbs selectively the glucose molecules by using the D-Galactose/D-Glucose Binding Protein, the effective mass of the micro-cantilever 4 alters by Δm, which in turn alters the resonance frequency of the sensor. However, the Δm has substantially no affection on the elastic constant k of the micro-cantilever 4 and can be omitted, thus, the change Δm of the effective mass of the micro-cantilever 4 may be expressed by $$\Delta m = \frac{k}{4\pi^2}\left(\frac{1}{f_1^2} - \frac{1}{f_o^2}\right) \quad (3)$$

It can be known from the above three equations (1), (2) and (3) that the change Δm of the effective mass of the micro-cantilever 4 depends on the Young Modulus and geometric parameters of the micro-cantilever 4.

However, because the structure of the micro-cantilever 4 is a composite structure which in fact includes three parts, that is, the silicon micro-cantilever 4, the gold film 5 and the D-Galactose/D-Glucose Binding Protein layer 11, it is necessary to calculate the total Young Modulus E and the effective mass $m_{eff}$ of the micro-cantilever by using Composite Film Structural Mechanics Theory after the D-Galactose/D-Glucose Binding Protein is bound, and to perform testing calibration on these parameters based on calculation by a mechanical testing apparatus, such as a nano-indenter, thereby accurate measurement of the mass of the glucose molecules is achieved.

Figure 4:
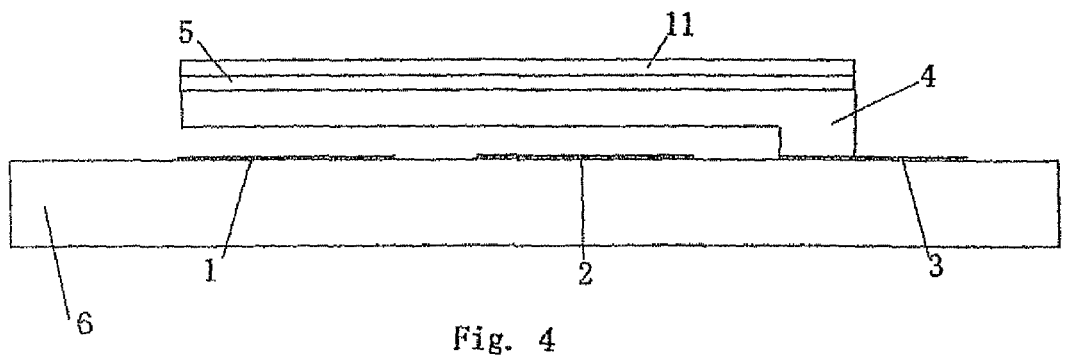
FIG. 4 is a section view schematically showing the structure of the micro-cantilever sensor in FIG. 1, wherein the D-Galactose/D-Glucose Binding Protein has been bound to the micro-cantilever sensor.

Specifically, after completing the design and manufacturing of the resonance-type micro-cantilever 4 and the micro fluid channel unit, completing the biosynthesizing and binding of the D-Galactose/D-Glucose Binding Protein, and completing the calibrating of the parameters of the resonance-type micro-cantilever glucose sensor having the bound D-Galactose/D-Glucose Binding Protein, the method for measuring the amount of an analyte to be detected, such as the glucose, in the human interstitial fluid according to the present invention comprises:

Step S10: Measuring a natural resonant frequency of the micro-cantilever of the resonance-type micro-cantilever glucose sensor having the bound D-Galactose/D-Glucose Binding Protein (as shown in FIG. 4), comprising:

Step S11: Applying an AC driving voltage between the driving electrode 1 on the first substrate 6 and the micro-cantilever electrode 3 so that the micro-cantilever 4 vibrates in the direction perpendicular to the first substrate 6;

Step S12: Measuring a change of capacitance between the detecting electrode 2 on the first substrate 6 and the micro-cantilever electrode 3 in real time during the micro-cantilever 4 vibrates; and Step S13: Scanning and adjusting a driving frequency of the AC driving voltage at a certain frequency interval in a way of frequency sweep while measuring the change of the capacitance in 312 in real time, wherein when the change of the capacitance is maximal, the micro-cantilever 4 is in a resonance state, in this case, the driving frequency $f_0$ of the AC driving voltage at which the change of the capacitance is maximal is determined as the natural resonant frequency of the micro-cantilever.

Figure 5:
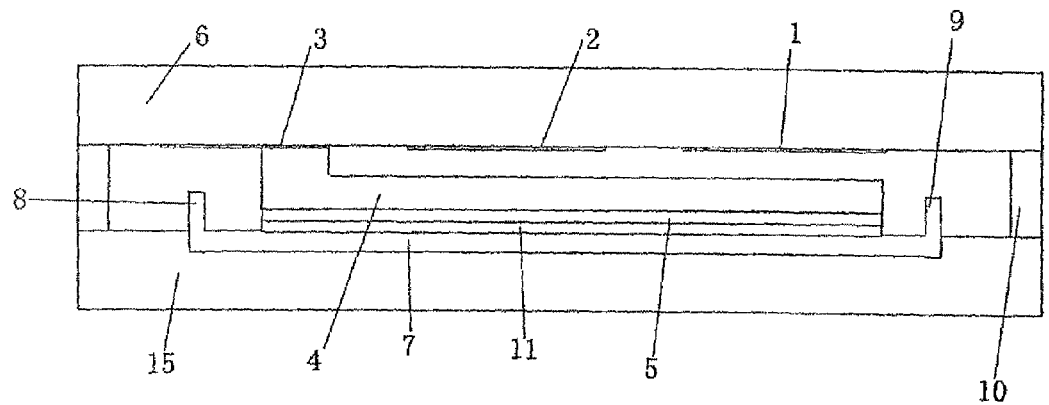
FIG. 5 is a section view schematically showing that the micro-cantilever sensor in FIG. 4 and the micro fluid channel unit in FIG. 2 are integrated to adsorb, at the surface of the gold film, an analyte to be detected, such as glucose, in human interstitial fluid.

Step S20: Stopping the electrostatic driving, and then overturning the sensor including the micro-cantilever 4 comprising the gold film 5 and the D-Galactose/D-Glucose Binding Protein. By using the micro fluid channel structure shown in FIG. 2, and though the V-shape self-alignment holes 14 formed on the first substrate 6 of the micro-cantilever sensor and the second substrate 15 of the fluid channel unit, the micro-cantilever sensor and the fluid channel unit are assembled together. The structure and the self-location assembling process of the V-shape self-alignment holes 14 are shown in FIG. 7. These V-shape self-alignment holes 14 may be formed by micromachining through an anisotropic vetch-stop technique. In addition, by providing the support posts 10 having a predetermined length between the first substrate 6 and the second substrate 10, the surface of the gold film 5 is allowed to be in close contact with the surface of the micro fluid channel 7, and thereby the structure shown in FIG. 5 is formed.

Step S30: By using the structure shown in FIG. 5, guiding the human interstitial fluid including the glucose molecules into the micro fluid channel via the micro pump in a way that the human interstitial fluid passes the surface of the D-Galactose/D-Glucose Binding Protein layer 11 at a stable or constant speed, thus, the glucose molecules in the human interstitial fluid are adsorbed to the surface of the D-Galactose/D-Glucose Binding Protein layer 11, and in this case, the substance composition and structure on the surface of the micro-cantilever sensor are shown in FIG. 6.

Step S40: Removing the micro fluid channel unit from the structure shown in FIG. 5, and the remained micro-cantilever sensor is the same as that in FIG. 4. It should be noted that the glucose molecule layer 13 is formed on the surface of the D-Galactose/D-Glucose Binding Protein layer 11 (referring to FIG. 6). Later, Steps S11-S13 are repeated to measure a new resonance frequency $f_1$ of the micro-cantilever 4 on which the glucose molecules are adsorbed.

Step S50: By using the above equation (3), calculating the mass of the glucose molecules in the human interstitial fluid which are adsorbed to the D-Galactose/D-Glucose Binding Protein layer 11.

Though the present invention discloses the resonance-type micro-cantilever glucose sensor which has the D-Galactose/D-Glucose Binding Protein bound thereon and which is used to measure the glucose concentration in the human interstitial fluid, the sensor may be extended to be a multi-sensor array structure comprising a plurality of the micro-cantilevers. Correspondingly, the micro fluid channel may be extended to be a multi-channel array structure, and proteins (or antibody-antigen) having selective adsorption ability for different substances may be bound to the surfaces of different micro-cantilevers. Further, this array-type micro-cantilever sensor may perform multi-parameter measurement so as to measure quickly other trace constituents or chemicals, in addition to the glucose, in the human interstitial fluid measure at one time.

Although several exemplary embodiments have been shown and described, it would be appreciated by those skilled in the art that various changes or modifications may be made in these embodiments without departing from the principles and spirit of the disclosure, the scope of which is defined in the appended claims and their equivalents.

The invention claimed is:

1. A sensor for measuring the amount of an analyte to be detected in human interstitial fluid, comprising a micro-cantilever sensing unit which includes:
    a first substrate;
    a micro-cantilever which is substantially in parallel with the first substrate and one end of which is supported onto the first substrate;
    a gold film formed onto at least one side of the micro-cantilever;
    a protein layer formed on the gold film to adsorb, at a surface thereof, the analyte to be detected in human interstitial fluid;
    a driving electrode provided on the first substrate;
    a micro-cantilever electrode which is provided on the first substrate at a position where the micro-cantilever is supported, and which is cooperated with the driving electrode so as to drive the micro-cantilever to produce resonance in a direction perpendicular to the first substrate; and
    a detecting electrode provided on the first substrate and cooperated with the micro-cantilever electrode to detect resonance frequency of the micro-cantilever.

2. The sensor according to claim 1, wherein the gold film is formed on a surface of one side of the micro-cantilever opposite to the other side thereof facing the first substrate.

3. The sensor according to claim 2, wherein the gold film is deposited, by means of a sputtering process or an evaporation process, on the surface of the micro-cantilever made of silicon.

4. The sensor according to claim 1, wherein the protein layer comprises D-Galactose/D-Glucose Binding Protein for selectively adsorbing glucose molecules in the human interstitial fluid.

5. The sensor according to claim 4, wherein the protein layer is adhered to a surface of the gold film by amine coupling or mercaptan coupling.

6. The sensor according to claim 1, wherein between the other side of the micro-cantilever facing the first substrate and the detecting electrode is formed a parallel plate capacitor.

7. A fluid channel unit comprising:
    a second substrate; and
    a fluid channel formed on the second substrate, wherein human interstitial fluid to be detected flows through the fluid channel in a way that the protein layer of the sensor for measuring the amount of an analyte to be detected in the human interstitial fluid according to claim 1 is brought in at least partial contact with a surface of the human interstitial fluid so that human interstitial fluid molecules of the human interstitial fluid are adsorbed onto the surface of the protein layer.

8. The fluid channel unit according to claim 7, wherein the surface of the gold film can be brought in at least partial contact with protein solution flowing in the fluid channel so as to form the protein layer on the gold film.

9. A method for measuring the amount of an analyte to be detected in human interstitial fluid, comprising steps of:
    measuring a natural resonant frequency of the micro-cantilever of the sensor for measuring the amount of an analyte to be detected in human interstitial fluid according to claim 1, comprising steps of:
        applying an AC driving voltage between the driving electrode and the micro-cantilever electrode to drive the micro-cantilever to vibrate in the direction perpendicular to the first substrate;
        measuring a change of capacitance between the detecting electrode on the first substrate and the micro-cantilever electrode in real time during the micro-cantilever vibrating; and
        determining the driving frequency of the AC driving voltage at which the change of the capacitance is maximal as a first resonance frequency $f_0$ of the micro-cantilever by adjusting a driving frequency of the AC driving voltage and repeating the capacitance measurement step, and;
    absorbing human interstitial fluid molecules of the human interstitial fluid onto the surface of the protein layer by bring fluid containing the human interstitial fluid in contact with the surface of the protein layer;
    measuring a second resonance frequency $f_1$ of the micro-cantilever on which the human interstitial fluid molecules have been adsorbed by repeating the applying voltage step, the measuring capacitance step and the determining resonance frequency step; and
    calculating the amount of the analyte to be detected in the human interstitial fluid based on the first resonance frequency $f_0$ and the second resonance frequency $f_1$.

10. The method according to claim 9, wherein in the absorbing step, the human interstitial fluid passes the protein layer in the flow channel of the fluid channel unit according to claim 7.

11. The method according to claim 9, further comprising a protein layer forming step which includes steps of:
    guiding a first chemical solution for activating a surface of the gold film into the fluid channel;
    flowing the first chemical solution through the surface of the gold film so as to activate the surface of the gold film and form a self-assembling molecule layer via Au—S bonds;
    guiding a second chemical solution for surface coupling and D-Galactose/D-Glucose Binding Protein into the fluid channel respectively;
    at a surface of the self-assembling molecule layer, securing the D-Galactose/D-Glucose Binding Protein to the activated surface of the gold film by using amine coupling or mercaptan coupling.

12. The method according to claim 11, wherein the D-Galactose/D-Glucose Binding Protein is a protein that adsorbs glucose molecules with selectivity.

13. The method according to claim 12, further comprising a protein synthesis step of forming the D-Galactose/D-Glucose Binding Protein, including:
    performing site-directed mutation on encoding gene mglB of the D-Galactose/D-Glucose Binding Protein of *escherichia coli*, wherein the mutation is actualized at E149 mutation site only, or both at E149C mutation site and atA213S mutation site, or simultaneously at E149, A213 and L238 mutation sites;
    constructing a gene engineering strain which over-expresses wild type D-Galactose/D-Glucose Binding Protein of the escherichia coli and mutation type D-Galactose/D-Glucose Binding Protein of the escherichia coli;
    fermenting the constructed gene engineering strain by using a shake flask so that the D-Galactose/D-Glucose Binding Protein is expressed stably; and
    separating and purifying the D-Galactose/D-Glucose Binding Protein from fermenting products.

14. A sensor system for sensing the amount of an analyte to be detected in human interstitial fluid, comprising:
    the sensor for measuring the amount of the analyte to be detected in the human interstitial fluid according to; and
    the fluid channel unit according to claim 7.

15. The sensor system according to claim 14, further comprising:
- at least two first self-alignment holes formed at two opposite ends of the first substrate;
- at least two second self-alignment holes formed at two opposite ends of the second substrate and corresponding to the first self-alignment holes respectively; and
- a plurality of support posts which are provided respectively within the self-alignment holes so that the sensor having the micro-cantilever is supported on the fluid channel unit and that protein solution flowing in the fluid channel is maintained to be in at least partial contact with a surface of the gold film.

* * * * *